(12) United States Patent
Cox et al.

(10) Patent No.: US 7,087,039 B1
(45) Date of Patent: Aug. 8, 2006

(54) PERFUSION BALLOON ANGIOPLASTY CATHETER

(75) Inventors: James E. Cox, Plymouth, MN (US); Richard G. Cornelius, Wayzata, MN (US); Tracee E. J. Eidenschink, Wayzata, MN (US); Gregory A. Boldenow, Crystal, MN (US); Brooke Q. Ren, Brooklyn Park, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 08/909,130

(22) Filed: Aug. 11, 1997

Related U.S. Application Data

(63) Continuation of application No. 08/612,061, filed on Mar. 7, 1996, now abandoned, which is a continuation-in-part of application No. 08/441,618, filed on May 15, 1995, now Pat. No. 5,591,129, which is a continuation-in-part of application No. 08/204,733, filed on Mar. 2, 1994, now abandoned.

(51) Int. Cl.
*A61M 29/00* (2006.01)
(52) U.S. Cl. .............. 604/96.01; 604/103.09; 606/194
(58) Field of Classification Search .......... 604/96–103, 604/265, 280, 165, 164, 96.01, 102.02, 102.03, 604/103.01, 164.01, 164.03, 165.01, 103.09; 606/191–194; 128/772
See application file for complete search history.

(56) References Cited

U.S. PATENT DOCUMENTS

| 3,585,983 | A | | 6/1971 | Kastrowitz et al. |
|---|---|---|---|---|
| 3,834,394 | A | | 9/1974 | Hunter et al. |
| 4,276,874 | A | | 7/1981 | Wolvek et al. |
| 4,362,150 | A | | 12/1982 | Lombardi, Jr. et al. |
| 4,402,307 | A | | 9/1983 | Hanson et al. |
| 4,444,186 | A | * | 4/1984 | Wolvek et al. .............. 606/194 |
| 4,581,017 | A | | 4/1986 | Sahota |
| 4,646,719 | A | | 3/1987 | Neuman et al. |
| 4,689,041 | A | | 8/1987 | Corday et al. |
| 4,744,366 | A | * | 5/1988 | Jang ........................... 606/194 |
| 4,771,777 | A | | 9/1988 | Horzewski et al. |
| 4,790,315 | A | | 12/1988 | Mueller, Jr. et al. |
| 4,820,349 | A | * | 4/1989 | Saab .......................... 128/344 |
| 4,877,031 | A | * | 10/1989 | Conway et al. .............. 606/194 |
| 4,892,519 | A | * | 1/1990 | Songer et al. .......... 604/102.03 |
| 4,921,483 | A | | 5/1990 | Wijay et al. |
| 4,944,745 | A | | 7/1990 | Sogard et al. |
| 5,000,734 | A | | 3/1991 | Boussignac et al. |

(Continued)

FOREIGN PATENT DOCUMENTS

EP 0 246 998 A2 11/1987

(Continued)

*Primary Examiner*—Nicholas D. Lucchesi
*Assistant Examiner*—Matthew DeSanto
(74) *Attorney, Agent, or Firm*—Crompton, Seager & Tufte LLC

(57) ABSTRACT

A balloon angioplasty catheter having a balloon head assembly carried at the distal end of an elongated catheter body. The balloon head assembly includes an inflatable balloon envelope and a perfusion lumen extending through the balloon envelope to provide a blood flow passage during inflation of the balloon envelope. The invention also encompasses embodiments having a collapsible guidewire lumen for increasing perfusion blood flow upon guidewire withdrawal. Also within the scope of the invention is a distally stepped down perfusion catheter, allowing for decreased distal cross section. In another preferred embodiment, the perfusion lumen is inflatable. In yet another embodiment, the guidewire lumen is external to the perfusion lumen.

1 Claim, 8 Drawing Sheets

U.S. PATENT DOCUMENTS

| | | | |
|---|---|---|---|
| 5,046,503 A | 9/1991 | Schneiderman | |
| 5,061,267 A * | 10/1991 | Zeiher | 606/40 |
| 5,087,244 A * | 2/1992 | Wolinsky et al. | 604/509 |
| 5,087,247 A | 2/1992 | Horn et al. | |
| 5,090,958 A * | 2/1992 | Sahota | 604/98.01 |
| 5,106,368 A * | 4/1992 | Uldall et al. | 604/43 |
| 5,114,423 A * | 5/1992 | Kasprzyk et al. | |
| 5,158,540 A | 10/1992 | Wijay et al. | |
| 5,160,321 A | 11/1992 | Sahota | |
| 5,195,971 A | 3/1993 | Sirhan | |
| 5,201,723 A | 4/1993 | Quinn | |
| 5,257,974 A * | 11/1993 | Cox | |
| 5,279,562 A | 1/1994 | Sirhan et al. | |
| 5,295,962 A * | 3/1994 | Crocker et al. | |
| 5,300,085 A * | 4/1994 | Yock | 606/191 |
| 5,318,535 A * | 6/1994 | Miraki | 604/103.1 |
| 5,338,300 A * | 8/1994 | Cox | |
| 5,344,402 A * | 9/1994 | Crocker | 604/103.01 |
| 5,378,237 A | 1/1995 | Boussignac et al. | |
| 5,383,890 A * | 1/1995 | Miraki et al. | 606/194 |
| 5,522,800 A * | 6/1996 | Crocker | |
| 5,542,926 A * | 8/1996 | Crocker | |
| 5,554,119 A * | 9/1996 | Harrison et al. | 604/103.01 |

FOREIGN PATENT DOCUMENTS

| | | |
|---|---|---|
| EP | 0 353 889 A1 | 2/1990 |
| EP | 0 441 384 A2 | 8/1991 |
| EP | 0 517 654 A2 | 12/1992 |
| EP | 0 629 417 A2 | 12/1994 |
| WO | WO 92/20398 | 11/1992 |

* cited by examiner

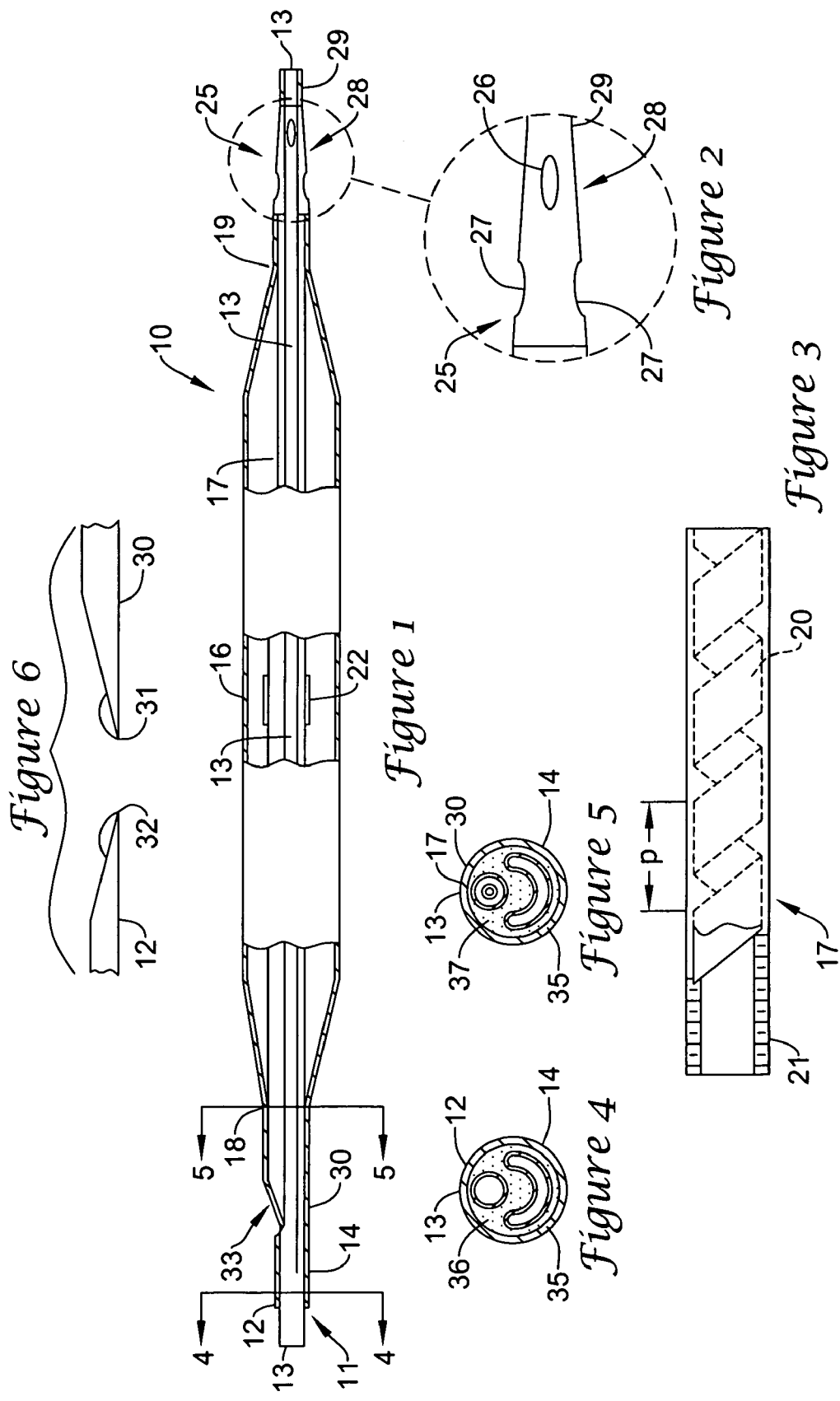

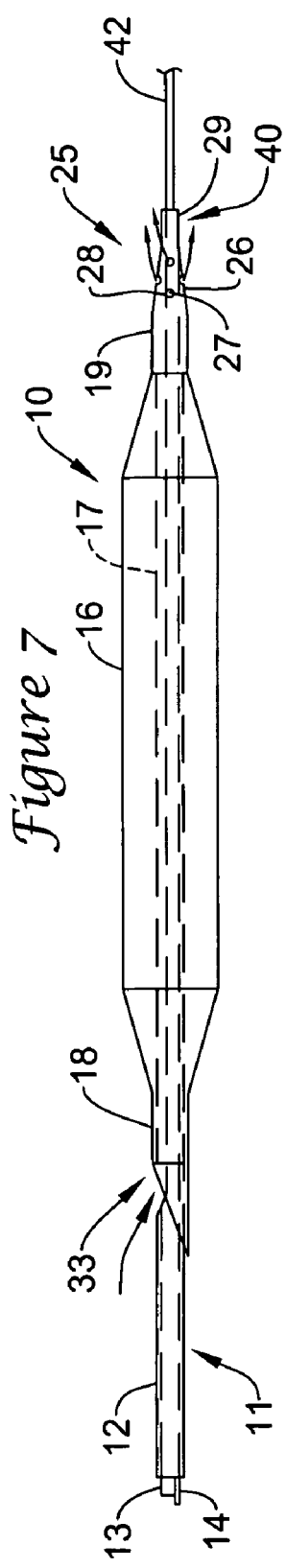
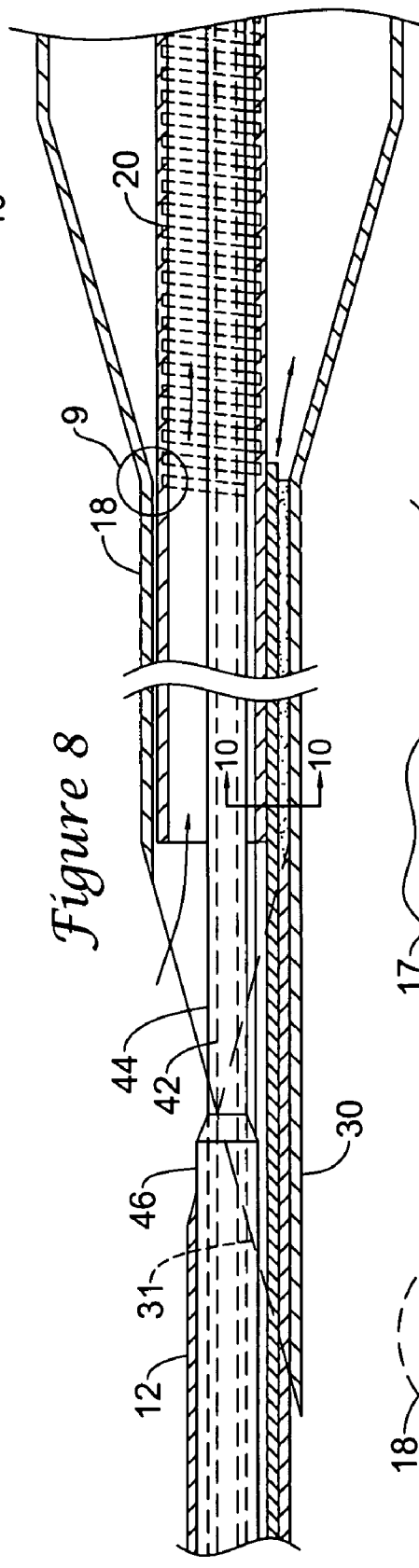
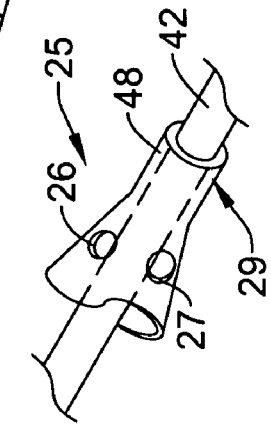
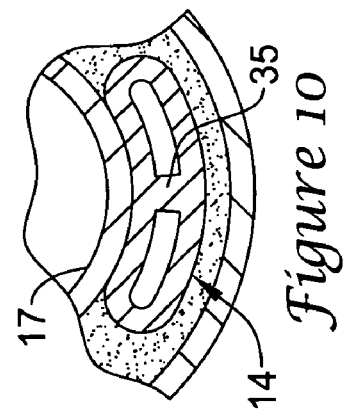
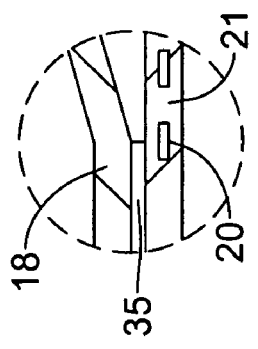

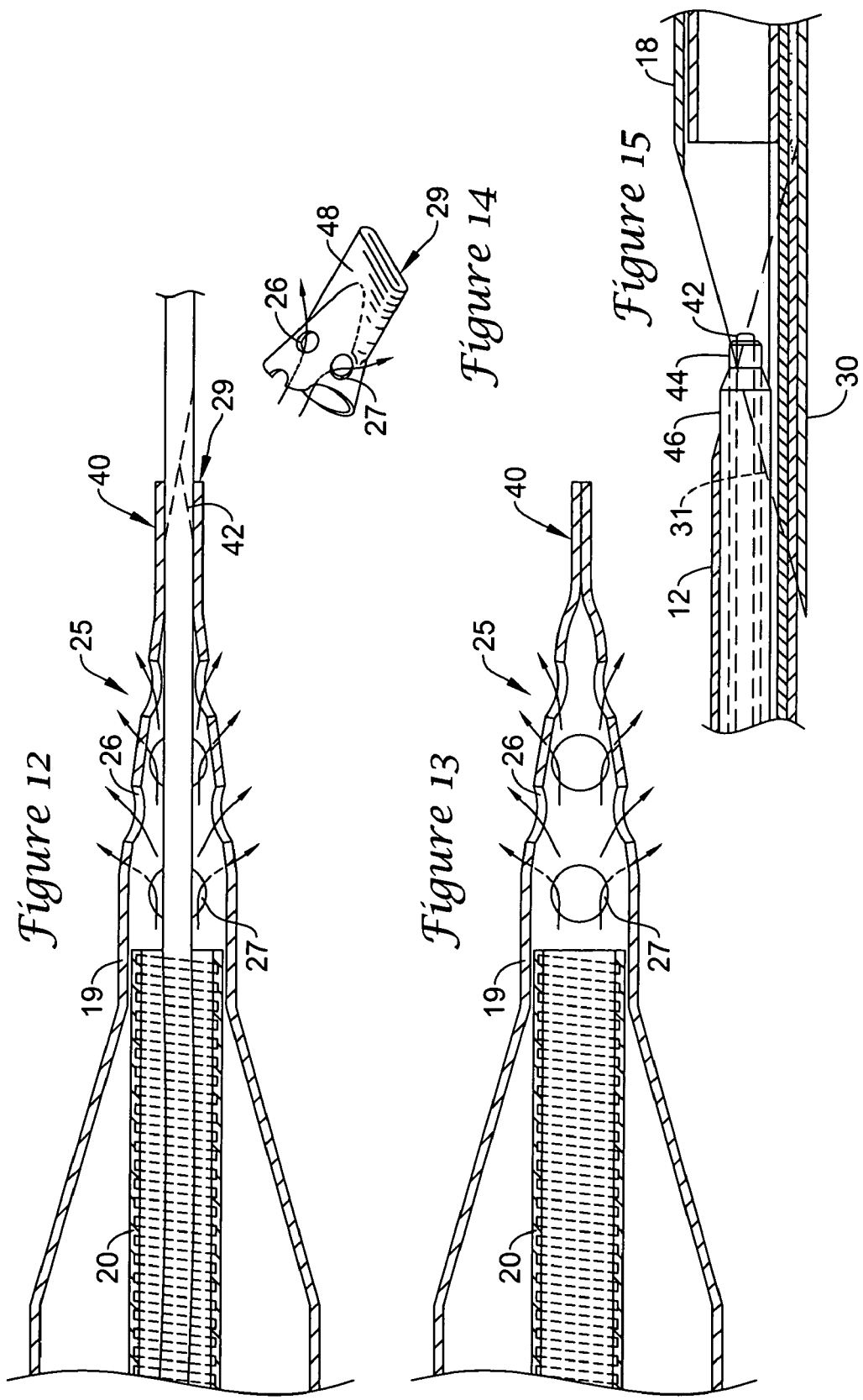

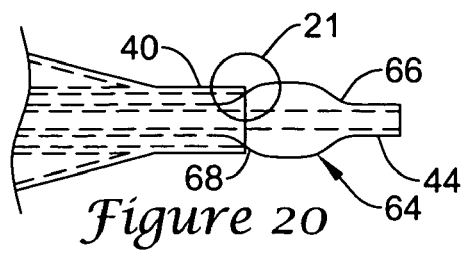
Figure 20
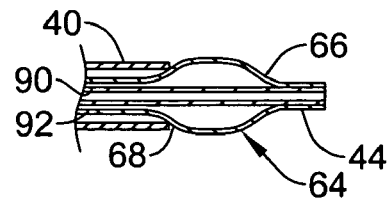
Figure 21
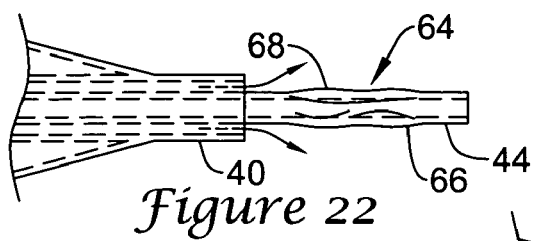
Figure 22
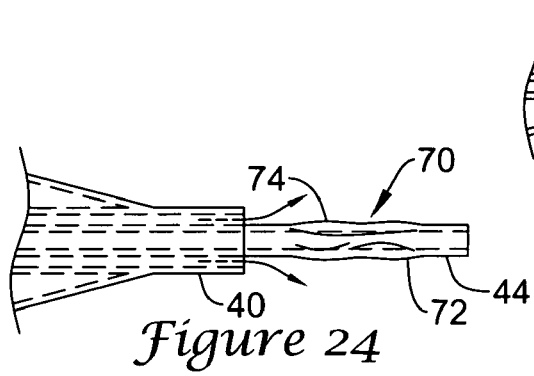
Figure 23
Figure 24
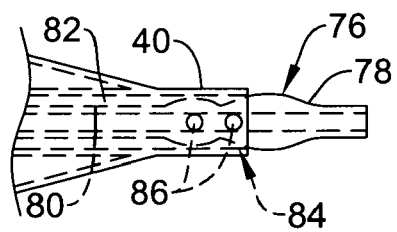
Figure 25
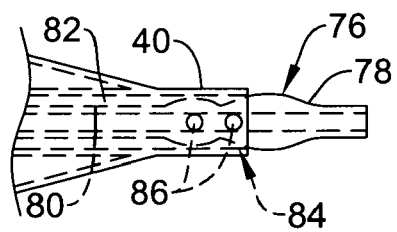
Figure 26
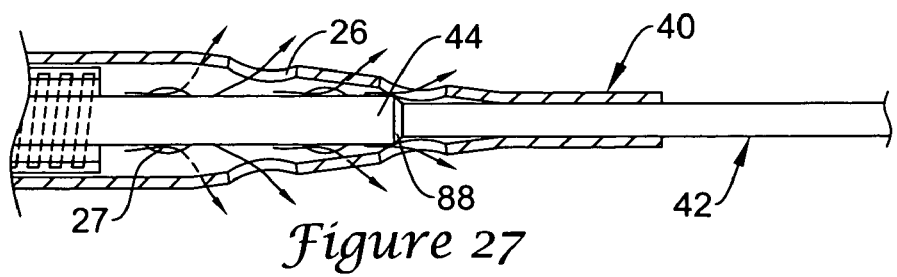
Figure 27

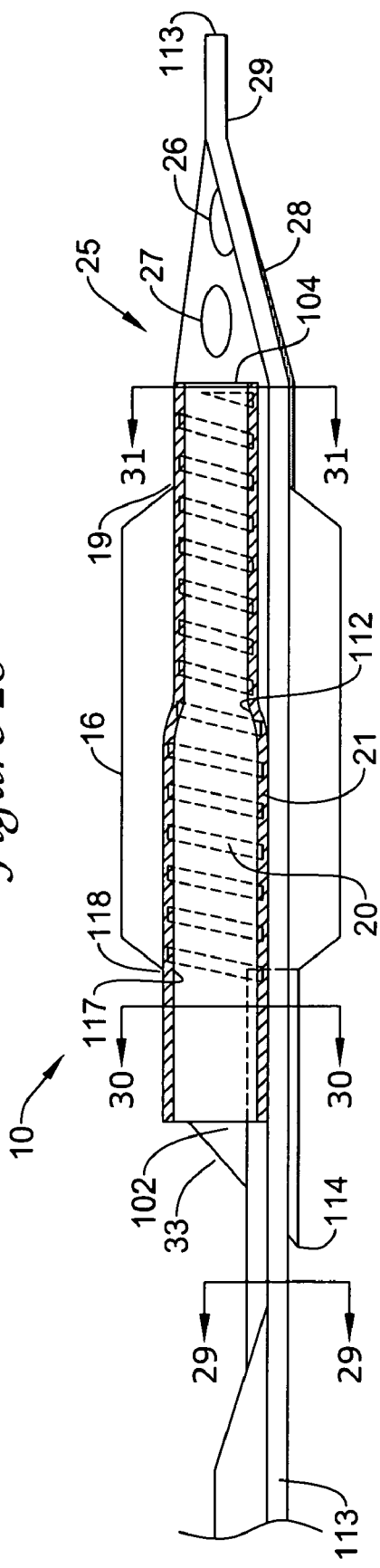
Figure 28
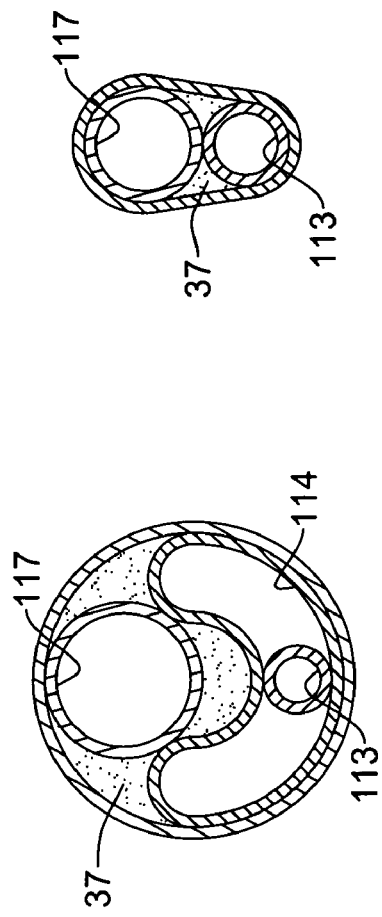
Figure 30
Figure 31
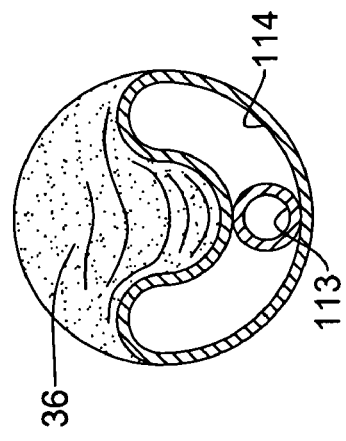
Figure 29

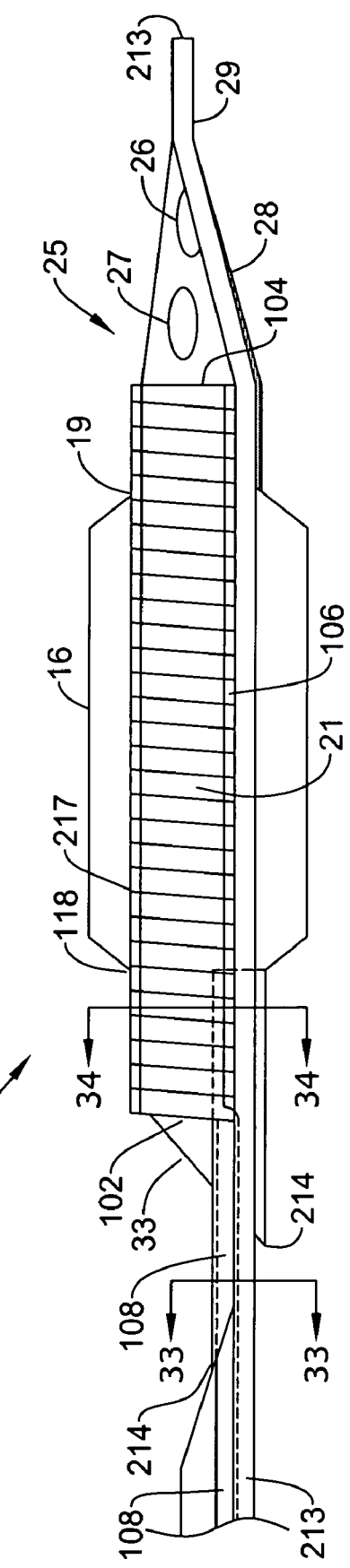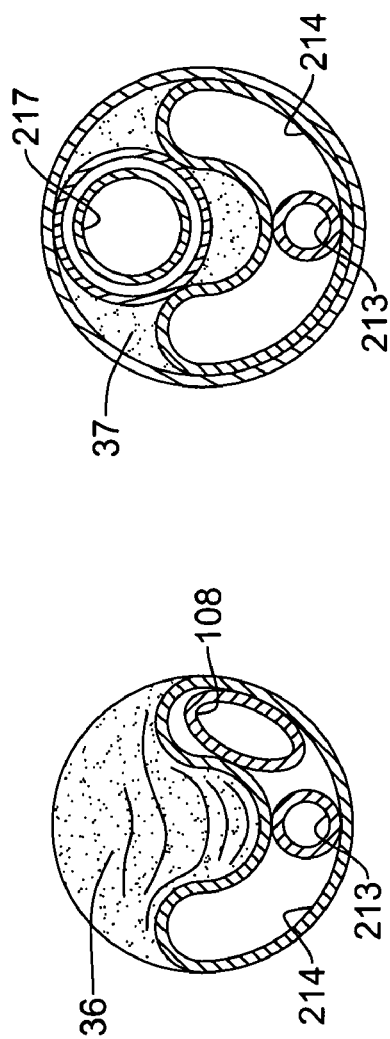
Figure 32
Figure 33
Figure 34

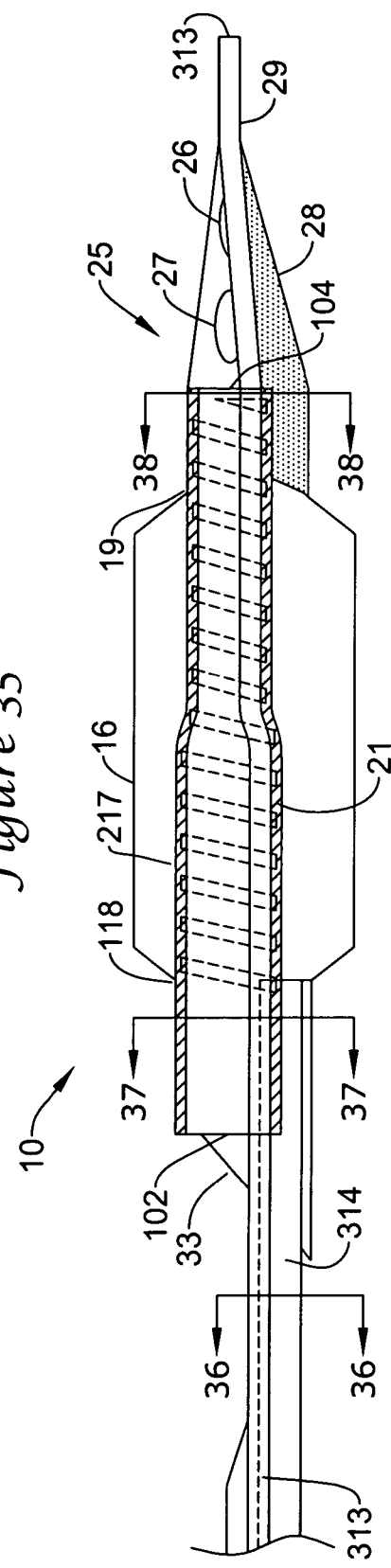
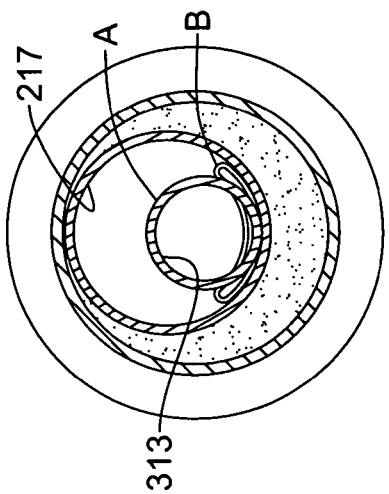
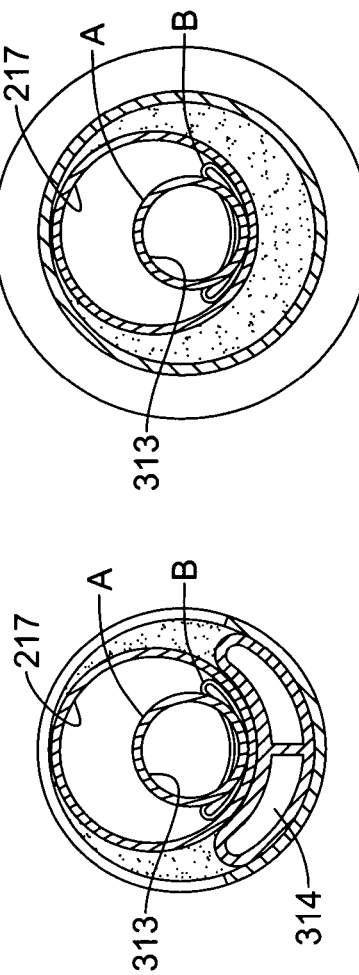
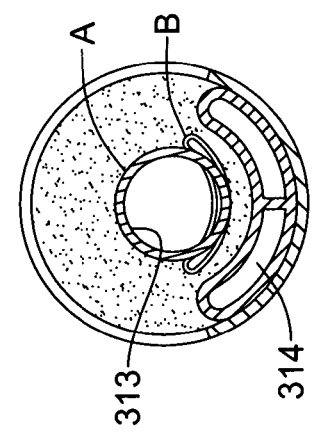

PERFUSION BALLOON ANGIOPLASTY CATHETER

CROSS REFERENCE TO RELATED APPLICATIONS

This application is a continuation of application Ser. No. 08/612,061, filed Mar. 7, 1996, now abandoned which is a continuation-in-part of application Ser. No. 08/441,618, filed May 15, 1995, now U.S. Pat. No. 5,591,129 which in turn is a continuation-in-part of application Ser. No. 08/204,733, filed Mar. 2, 1994, now abandoned.

BACKGROUND OF THE INVENTION

The present invention relates to angioplasty and, in particular, to perfusion balloon angioplasty catheters.

Balloon catheters are widely used in a variety of intravascular applications. In particular, angioplasty has gained wide acceptance as an efficient and effective treatment for particular vascular conditions. For example, angioplasty is widely used to treat stenoses in coronary arteries, although its application to stenoses in other parts of the vascular system is also known.

The most common form of angioplasty is percutaneous transluminal coronary angioplasty (PTCA) which utilizes a dilatation catheter having an inflatable balloon at its distal end. The catheter is guided through the vascular system, using fluoroscopy, until the balloon is positioned across the stenosis. The balloon is then inflated such that the balloon engages the stenosis to reestablish acceptable blood flow through the artery.

An initial concern with PTCA was the temporary blockage of blood flow during balloon inflation. With increasing clinical experience, this concern declined. The vast majority of patients tolerate 30–60 second dilatations quite well. Concurrently, cardiologists discovered that prolonged dilatations can assist with some developments occasionally encountered with angioplasty. For example, prolonged dilatations of several minutes may be employed on the occurrence of dissections, intimal flaps, acute thrombolysis and vessel spasms. The profound ischemia of long dilatation is outweighed by the potential prevention of emergency coronary bypass surgery.

A variety of techniques have been proposed to facilitate prolonged dilatations. These include the use of pharmacologic agents to improve myocardial tolerance of ischemia, synchronized retroperfusion, mechanical pump distal perfusion and auto or passive perfusion.

The use of pharmacologic agents treats the symptoms of ischemia without addressing the cause. As a result, this approach is inherently limited.

Synchronized retroperfusion involves pumping blood during diastole into the coronary sinus and then subselectively into the regional coronary veins which drain the jeopardized myocardium. While this approach potentially offers nearly complete myocardial perfusion, it is complicated and cumbersome.

Mechanical pump distal perfusion involves pumping blood (or other perfusate) through a lumen of the PTCA catheter. As the name implies, this requires some form of mechanical pump which complicates the angioplasty equipment and procedure.

Auto or passive perfusion has found increasing interest both for prolonged dilatations as well as shorter dilatations having a duration on the order of non-perfusion dilatations. Typically, in passive perfusion, the balloon catheter acts as temporary stent. That is, a perfusion lumen is employed to provide a blood flow passage during balloon inflation. Typically, the perfusion lumen extends through the balloon envelope having an inlet proximal to the balloon envelope and a discharge distal to the balloon envelope. Proposed inlet configurations have included side openings in the catheter as well as a beveled opening to the blood flow channel. Proposed discharge configurations have included a main axial orifice and side openings. Clearly, the inlet and outlet have a direct effect on blood flow capacity. Further, pressure within the balloon envelope during balloon inflation has a tendency to compress a perfusion lumen within the envelope thereby potentially constricting the blood flow passage. On the other hand, countering this tendency by stiffening the perfusion lumen walls can seriously impact trackability of the catheter itself. The attachment of a projecting distal tip to provide side wall discharge can affect trackability as a result in changes of stiffness from material changes and/or the attachment itself.

As discussed above, various proposed discharge configurations have included a main axial orifice and side openings. For a number of reasons, including trackability, it is desirable to be able to control relative egress flow through the main axial orifice and the side openings. Such control can increasingly be a factor when perfusion flow is maximized, for example, where the guidewire along which the catheter is inserted is withdrawn after catheter insertion in order to increase the cross-sectional flow area through the perfusion lumen of the catheter which passes through the balloon envelope.

It is desirable to maximize flow through the perfusion lumen by having a perfusion lumen with large cross sectional area. It is also desirable to have a balloon catheter head with small cross sectional area to allow for inserting the distal tip through narrowed stenotic regions. It would be advantageous to have a catheter maximizing both of these seemingly conflicting goals.

It is to these dictates of the prior art that the present invention is directed. It is a balloon angioplasty catheter which serves to obviate many of the shortcomings of prior art structures.

SUMMARY OF THE INVENTION

The present invention provides a perfusion balloon catheter particularly adapted to angioplasty of the type having a balloon assembly carried at the distal end of an elongated catheter body. The balloon assembly includes an inflatable balloon envelope and a perfusion lumen extending through the balloon envelope to provide a blood flow passage during inflation of the balloon envelope. In a preferred embodiment, the perfusion lumen is formed of an encapsulating flexible material supported against collapse during balloon inflation by a helical member having spaced coils. The pitch of the spaced coils may be selected to avoid coil-to-coil contact during traverse of a body vessel, as during advance of the catheter through the vascular system during delivery of the catheter to a desired site within the vessel. Blood flow through the perfusion lumen is facilitated in accordance with another aspect of the present invention through side opening configurations which facilitate discharge during perfusion. In a preferred embodiment, the discharge is through generally oval orifices. The orifices are located in a distally projecting tip, the tip being in fluid communication with the perfusion lumen. In a preferred embodiment, the major dimension of the oval orifices is generally aligned with the direction of projection of the projecting tip.

To negate the effect on trackability of stiffness transitions within the balloon head assembly, the present invention provides an integral projecting tip. That is, the balloon envelope and projecting tip of the balloon head assembly are integrally formed. In a preferred embodiment, a plurality of discharge orifices extend through the projecting tip side wall.

In some embodiments, various means can be provided for facilitating preferred discharge through the side opening orifices. Various embodiments of the invention provide different means for accomplishing this. For example, in one embodiment, a gate normally biased to a closed position, is provided at a distal end of the discharge lumen. During catheter installation, the guidewire and an axially displaceable guidewire tube disposed radially intermediate the guidewire and an axially fixed guidewire tube, pass through the gate. After installation is completed, the guidewire and axially displaceable tube can be withdrawn to increase perfusion flow through the perfusion lumen. Upon withdrawal of the guidewire and displaceable tube, the gate, being biased to the closed position, will close in order to direct egress flow through the side orifices.

In other embodiments various other valving/metering structures are employed. In a number of embodiments of the invention, a valve member is carried by the axially displaceable guidewire tube so that, as that tube is moved axially through the discharge lumen, the location of the valve member relative to the discharge lumen distal end main axial orifice can be varied in order to control egress flow. When the valve member is fully closed, all flow will be directed through the side orifices. When the valve member is opened, egress flow will be divided between the side orifices and the main axial orifice.

While it is desirable to have a large perfusion lumen cross section so as to maximize blood flow, it is also desirable to have a small balloon catheter cross section so as to allow the balloon to pass through narrowed vessel regions. Several embodiments of the present invention address these conflicting goals.

One embodiment of the invention allows for a smaller balloon catheter cross section by having the perfusion lumen proximal end be of large cross section, decreasing to a smaller cross section at the distal end. The smaller cross section at the distal end allows inserting the distal end of the balloon catheter into narrowed vessel regions, without unduly restricting blood flow through the perfusion lumen.

Another embodiment of the present invention allows for increasing blood flow through the perfusion lumen by having the guidewire lumen external to the perfusion lumen. By having the guidewire lumen outside of the perfusion lumen, the cross sectional area available for blood flow inside the perfusion lumen is increased.

Yet another embodiment of the present invention provides for a collapsible guidewire lumen. After inserting the balloon catheter over a guidewire, the guidewire may be backed out, thereby allowing the guidewire lumen to collapse. This collapse increases the cross sectional area available for blood flow in the perfusion lumen.

In yet another embodiment of the present invention, the perfusion lumen wall is supported by inflatable coil members. The balloon catheter has a reduced cross section when the perfusion lumen coil members are deflated. This allows the catheter to be more easily advanced into a narrow vessel region. When the balloon distal tip is in position, the perfusion lumen coil members are inflated, increasing the perfusion lumen cross section. The inflation pressure provided to the perfusion lumen must be sufficient to support the perfusion lumen against the pressures of the balloon inflation fluid when the balloon is inflated.

The present invention is thus an improved balloon angioplasty catheter. More specific features and advantages obtained in view of those features will become apparent with reference to the DETAILED DESCRIPTION OF THE INVENTION, accompanying drawing figures, and appended claims.

BRIEF DESCRIPTION OF THE DRAWINGS

FIG. 1 is a partial cut-away including a balloon head assembly in accordance with the present invention;

FIG. 2 is an enlarged view of the indicated portion of FIG. 1;

FIG. 3 is a partial cutaway of an enlarged view of a portion of a perfusion lumen in accordance with the present invention;

FIG. 4 is a cross section taken along the line 4—4 in FIG. 1;

FIG. 5 is a cross section taken along the line 5—5 in FIG. 1;

FIG. 6 is an exploded view illustrating the manner of connection of the balloon head assembly to the distal end of the catheter body of the embodiment of FIG. 1;

FIG. 7 is a side elevational view of another embodiment of the balloon catheter;

FIG. 8 is a greatly enlarged fragmentary detail thereof sectioned vertically along the longitudinal axis and having some parts unsectioned for clarity;

FIG. 9 is a fragmentary detail thereof and enlarged therefrom in the area encircled at 9 in FIG. 8;

FIG. 10 is a greatly enlarged fragmentary detail view thereof taken generally along line 10—10 in FIG. 8;

FIG. 11 is a greatly enlarged fragmentary perspective detail thereof showing the distal end of the catheter balloon tip having the guidewire protruding through;

FIG. 12 is a fragmentary detail thereof sectioned vertically along the longitudinal axis and showing the guidewire protruding through distal end thereof;

FIG. 13 is a view similar to that of FIG. 12 showing guidewire withdrawn;

FIG. 14 is a view similar to that of FIG. 11 having guidewire withdrawn;

FIG. 15 is a greatly enlarged fragmentary detail thereof sectioned vertically along the longitudinal axis showing the guidewire and axially displaceable guidewire tube withdrawn;

FIG. 20 is a view similar to FIG. 18 illustrating another valving embodiment;

FIG. 21 is a greatly enlarged fragmentary detail view showing the construction of the valving structure;

FIG. 22 is a view similar to FIG. 19 showing the additional valving embodiment with the distal end of the catheter open;

FIG. 23 is similar to FIGS. 18 and 20 showing a further valving embodiment;

FIG. 24 is a view similar to FIGS. 19 and 22 showing the valving embodiment of FIG. 23 in an open disposition;

FIG. 25 is a view similar to FIGS. 18, 20, and 23 showing an additional valving embodiment;

FIG. 26 is a view similar to FIGS. 19, 22, and 24 showing the valving embodiment of FIG. 25 in an open disposition;

FIG. 27 is a view similar to FIGS. 12 and 13 illustrating an additional valving method;

FIG. 28 is a partial cut-away illustrating an embodiment having a guidewire lumen external to the perfusion lumen, and a stepped down perfusion lumen;

FIG. 29 is a cross section taken along the line 29—29 in FIG. 28;

FIG. 30 is a cross section taken along the line 30—30 in FIG. 28;

FIG. 31 is a cross section taken along the line 31—31 in FIG. 28;

FIG. 32 is a partial cut-away illustrating an embodiment having a collapsible guidewire lumen;

FIG. 33 is a cross section taken along the line 33—33 in FIG. 32;

FIG. 34 is a cross section taken along the line 34—34 in FIG. 32;

FIG. 35 is a partial cut-away illustrating an embodiment having an inflatable perfusion lumen and a stepped down perfusion lumen;

FIG. 36 is a cross section taken along the line 36—36 in FIG. 35;

FIG. 37 is a cross section taken along the line 37—37 in FIG. 35; and

FIG. 38 is a cross section taken along the line 38—38 in FIG. 35.

DETAILED DESCRIPTION OF THE INVENTION

Figure 16:
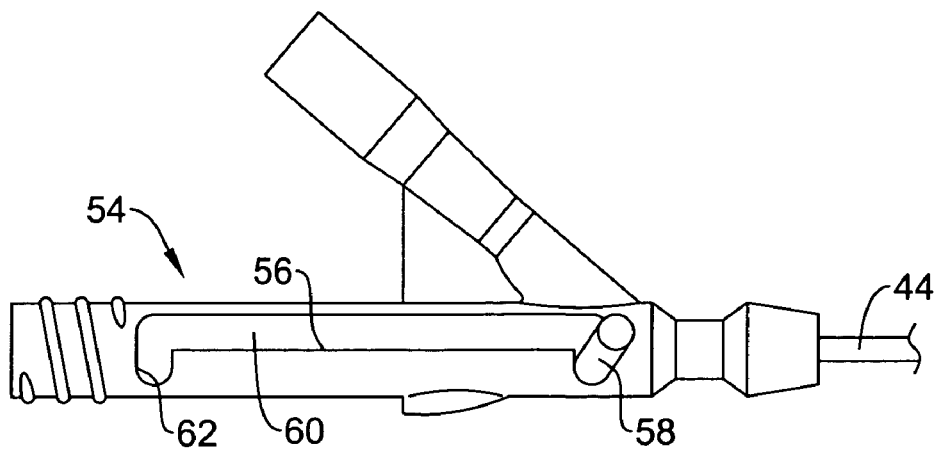
FIG. 16 is a fragmentary side elevational view of a manipulator at the proximal end of the catheter wherein the axially displaceable guidewire tube is extended.

FIG. 1 is a partial cut-away of a preferred embodiment of the present invention including a balloon head assembly generally designated at 10, the balloon head 10 being carried at the distal end 11 of an elongated catheter body (partially shown). The embodiment illustrated in FIG. 1 is an over-the-wire angioplasty balloon catheter. The distal terminus 11 of the catheter body includes an outer tubular member 12 surrounding an inner tubular guidewire lumen 13. The space between the outer surface of the guidewire lumen 13 and the inner surface of tubular member 12 provides a passage (an inflation lumen) for inflation of the balloon of balloon assembly 10, in known manner. In the illustrated embodiment, the tubular members 12 and 13 may be formed of polyethylene, for example, while those portions of the catheter body which are not illustrated may be of any conventional design, including a manifold. Fluid communication between the inflation lumen formed by the members 12 and 13 and the interior of the balloon of balloon assembly 10 is via a molded member 14 described more fully below. Molded member 14 may be extruded using polypropylene or polyethylene, for example, or otherwise molded of any suitable material.

Balloon assembly 10 includes a balloon envelope 16 which may be formed of a polyethylene/EVA blend, for example. A perfusion lumen 17 extends through the interior of the balloon envelope 16 from a proximal balloon waist 18 to a distal balloon waist 19. The perfusion lumen 17 is partially illustrated in FIG. 3 and is formed of a helical member 20 having spaced coils, the coils being encapsulated within and supporting a flexible material 21 such as urethane. In FIG. 3, the flexible material 21 is partially cut away with the member 20 being shown in phantom where it is encapsulated. The interior of the lumen 17 provides a blood flow passage through the interior of the balloon envelope—from proximal waist 18 to distal waist 19. The coil member 20 supports the lumen against collapse during inflation of the balloon envelop while the spacing of the coils is selected to avoid coil-to-coil contact during traverse of a body vessel. That is, particularly during advance of the catheter over a positioned guidewire, trackability of the catheter assembly is particularly important. The spacing of the coils (their "pitch" represented at "p" in FIG. 3) allows the inflation lumen 17 to flex through bends in the vessel being traversed due to the flexibility of the encapsulating material 21 while supporting that material against collapse during balloon inflation. Determination of coil pitch is within the skill of one ordinarily skilled in the art being dependent, to some extent, on the intended placement site of the balloon along the vessel (and the characteristics of the vessel to be traversed) and the support requirements of the encapsulating material 21. In a preferred embodiment, the helical member 20 is a ribbon of a suitable metal, surgical grade stainless steel, for example, having a thickness of 0.0015", a width of 0.015" and a pitch of 0.008" to 0.010". The helical member 20 may be radiopaque or alternatively, a marker band 22 may be provided, in known manner. The use of an encapsulated coil provides a thinner sidewall than would be the case with a solid wall tube layered with a coil which, in turn, allows a smaller balloon head profile.

A balloon assembly tip 25 extends distally from the balloon envelope and the distal end of perfusion lumen 17 and defines a discharge lumen therein. The projecting tip 25 is provided with a plurality of discharge orifices 26 and 27 (see FIG. 2) through its side wall. In a preferred embodiment, a first "stage" of three orifices 27 (two being visible in FIG. 2) are positioned equidistantly around the side wall of projecting tip 25 with a second "stage" of orifices 26 being positioned distally from the first stage formed by orifices 27. In the illustrated embodiment, there are three second stage orifices 26 (one being visible in FIG. 2) positioned equidistantly around the tip 25, each being positioned angularly intermediate the orifices 27 of the first stage. In the illustrated and described embodiment, the orifices of each stage are positioned around the tip 120° from the other orifices of their stage, with the orifices of one stage being offset by 60° from the orifices of the other stage.

To facilitate the discharge of flow through the perfusion lumen 17, the side, or side wall, orifices 26 and 27 may be elongated in the direction of extension of the projecting tip 25 and its interior discharge lumen. In the illustrated embodiment, this direction corresponds generally to the flow direction through the perfusion lumen 17. In a preferred embodiment, the orifices 26 and 27 are oval and have an aspect ratio of 1.5 to 1. To further facilitate discharge, the elongated tip 25 is provided with a portion 28 which converges distally, the orifices 26 and 27 passing through the side wall of the converging tip portion 28. The use of elongated orifices through the side wall of a converging tip has been found to significantly increase the flow through the perfusion lumen 17. The terminus 29 of the projecting tip 25 is generally cylindrical.

As described above, the catheter body includes a guidewire lumen 13. The guidewire lumen 13 extends from the catheter body and through the balloon assembly, including the balloon envelope, to terminate within the generally cylindrical portion 29 of projecting tip 25. The guidewire lumen 13 may be stepped down or otherwise decreased in size to facilitate reduction in the profile of the balloon assembly 10, in known manner. The guidewire lumen 13 extends through the perfusion lumen 17 and is bonded, in known manner, within the terminus 29 of projecting tip 25. The interior of projecting tip 25 forms a discharge lumen in fluid communication with the distal end of the perfusion lumen 17 (generally at waist 19) while the bonding of the guidewire lumen 13 at distal tip 29 prevents axial discharge of flow passing through the perfusion lumen 17.

Balloon waist 18 is generally cylindrical. Balloon assembly 10 further includes a generally cylindrical proximal extension from waist 18 indicated generally at 30. Extension 30 is skived (see FIG. 6) as indicated at 31. Similarly, tubular member 12 is generally cylindrical and is skived as indicated at 32. Extension 30 is larger than tubular member 12 such that member 12 may be positioned within, and bonded to the skived portion of projection 30, so as to provide a blood flow inlet indicated generally at 33 in FIG. 1. Blood flowing through the inlet passes through the extension 30 to the proximal terminus of perfusion lumen 17 (generally at waist 18). Blood passing through perfusion lumen 17 enters the discharge lumen of projection 25 to be discharged through the orifices 26 and 27.

As described above, molded member 14 extends from the inflation lumen between guidewire lumen 13 and tubular member 12 to the interior of the balloon envelope 16. Member 14 has a divided interior flow lumen or passage for inflation fluid (see FIGS. 4 and 5) the division in the flow lumen of member 14 resulting from the provision of a web 35 which acts to prevent the expansion of the member 14. As illustrated in FIG. 4, the member 14 and guidewire lumen 13 are bonded in a matrix of bonding material 36 at the terminus of the elongated catheter body 11, the bonding material 36 sealing the inflation lumen between the guidewire lumen 13 and sheath 12 of the catheter body. Similarly, the interior of the extension 30 opens to the interior of the flow lumen 17 (the guidewire lumen 13 being positioned within the perfusion lumen 17) with the member 14 extending beyond waist 18 into the interior of the balloon envelope. At the region of the waist 18, a matrix of bonding material 37 seals the interior of the balloon envelope 16 (see FIG. 5).

FIGS. 7–17 and 27 illustrate an additional embodiment encompassed by the present invention. In many respects, the additional embodiment is similar to, or the same as, the embodiment described with reference to FIGS. 1–6, including the use of an integrally formed, i.e. made from one piece as shown in FIGS. 1 and 7, balloon/projecting tip assembly. Consequently, only differences between the embodiments will be described with reference to FIGS. 7–14.

In the first embodiment described herein, the guidewire extends through an axially fixed guidewire tube 46, through the balloon envelope 16, and into and including the discharge lumen 40. The guidewire 42 of this embodiment extends through an axially positionable guidewire tube 44 which, in turn, extends through the fixed guidewire tube 46, and through the balloon envelope 16 and into the discharge lumen 40. Fixed tube 46 has a distal end which terminates just prior to the proximal perfusion opening. FIG. 11 illustrates guidewire 42 as extending through discharge lumen 40 forming the distal end of balloon assembly tip 25. As best illustrated in FIG. 8, the fixed guidewire tube 46 is mounted concentrically about the axially displaceable guidewire displaceable tube 44, and relative telescoping movement of the displaceable tube 44 with respect to the fixed tube 46 is permitted. The fixed tube 46, as can be seen, obviously has a diameter which is larger than that of the displaceable tube 44, and displaceable tube 44 has a diameter which is larger than that of guidewire 42.

As previously discussed in this document, under certain circumstances it is advantageous not only to minimize the length of time during which blood flow during dilatation might be occluded, but also to maximize perfusion when perfusion is afforded. To facilitate maximization of perfusion, once the catheter has been installed at a desired location, displaceable tube 44 could be withdrawn from the perfusion lumen 17 and into the fixed tube 46. Because the guidewire 42 is unconstrained by displaceable tube 44, the cross-sectional area of the perfusion lumen 17 will be significantly increased in view of the absence of displaceable tube 44. Perfusion will be increased commensurately.

In some cases, it might be desirable to occlude or at least minimize egress of perfused blood through the main axial orifice at the distal end of the discharge lumen 40 defining the balloon assembly tip 25. In the embodiment of FIGS. 7–17 and 27, the guidewire 42 is shown as passing through the balloon assembly tip discharge lumen 40. With the guidewire 42 in this position, perfusion will pass primarily through the side wall orifices 26, 27. If the guidewire 42 is withdrawn, however, a gate (as seen at 48) defined by the distal end of the discharge lumen 40 can be made to close automatically. This can be accomplished by making the distal end of the discharge lumen 40 from a resilient material and pre-biasing it to a closed position as best seen in FIG. 14. Initial passage of the guidewire 42 through the discharge lumen 40 will effect overcoming of this bias to enable passage of the guidewire 42 through the discharge lumen 40. Once the guidewire 42 is withdrawn, however, the gate 48 will return to its normally closed disposition so that perfused fluid will pass through the side wall orifices 26, 27. As discussed hereinbefore, FIG. 14 illustrates gate 48 as being in a closed disposition. In this disposition, gate 48 will substantially preclude flow of perfused blood through the main axial orifice at the distal end of the discharge lumen 40. It will be understood, however, that, for example, the structure illustrated in FIG. 11, wherein guidewire 42 passes through gate 48, flow of perfused blood through the main axial orifice at the distal end of the discharge lumen 40 will also be precluded. With guidewire 42 left in place, therefore, as illustrated in FIG. 11, perfusion will pass primarily through the side wall orifices 26, 27 also.

Figure 17:
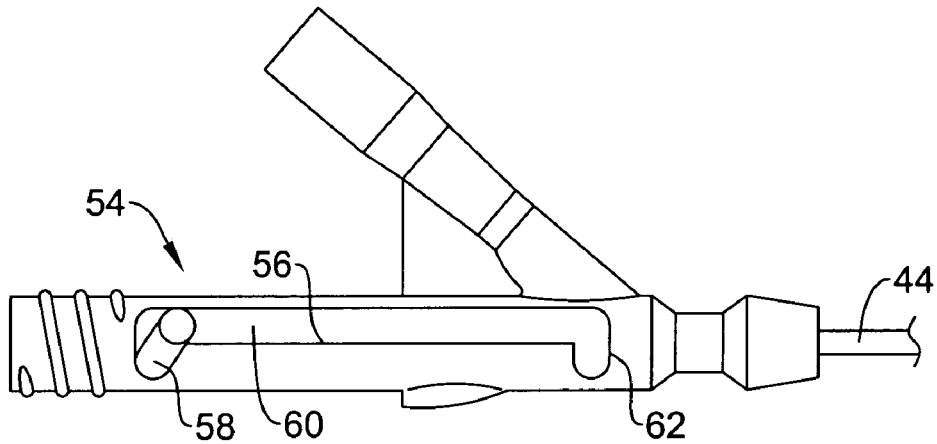
FIG. 17 is a fragmentary side elevational view of a manipulator at the proximal end of the catheter wherein the axially displaceable guidewire tube is withdrawn.

FIGS. 16–17 illustrate structure, disposed external to the patient upon which angioplasty were being performed, for controlling the axial positioning of the displaceable guidewire tube 44. These two figures show a handle 54 having an axial slot 56 formed therein. A pin 58 extends radially outwardly from a sleeve 60, received within the handle 54 and attached, either directly or indirectly, to the displaceable guidewire tube 44. The pin 58 is movable along the slot 56 to effect extension or withdrawal of the displaceable guidewire tube 44 to accomplish axial movement thereof. As seen in FIGS. 16 and 17, both ends of the slot are provided with 90° turns 62 within which the pin 58 can be captured in order to maintain displaceable guidewire tube 44 at a desired defined axial location. In the case of the pin position illustrated in FIG. 16, the displaceable guidewire tube 44 would be extended. With the pin 58 in the location as illustrated in FIG. 17, the tube 44 would be retracted into fixed guidewire tube 46.

FIG. 27 illustrates, with more specificity, a preferred structure of the axially displaceable guidewire tube 44. As can be seen in this figure, the displaceable guidewire tube 44 can be axially extended so that a distal, beveled end 88 of the tube 44 can engage the proximal end of the discharge lumen 40 to alter perfusion flow outwardly through lumen 40 and allow wire backloading by sealing the interface between beveled end 88 and the proximal end of discharge lumen 40.

It will be understood that, when the guidewire 42 is constrained by a displaceable guidewire tube 44 along its run through perfusion lumen 17, perfusion still could be increased when the guidewire 42 is withdrawn. This would be accomplished by making the displaceable guidewire tube 44 collapsible so that the cross-sectional area of the collapsed guidewire tube 44 would be significantly smaller than the cross-sectional area of the displaceable guidewire tube 44 when it constrains the guidewire 42. In the case of a collapsible displaceable guidewire tube 44, while perfusion will not be increased to the degree that it would when the displaceable guidewire tube 44 is retracted, perfusion would be significantly increased.

Figure 18:
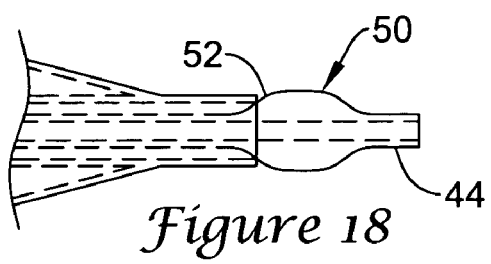
FIG. 18 is a fragmentary side elevational view of an alternate embodiment having the axially displaceable guidewire tube retracted to valve the distal end of catheter closed.
Figure 19:
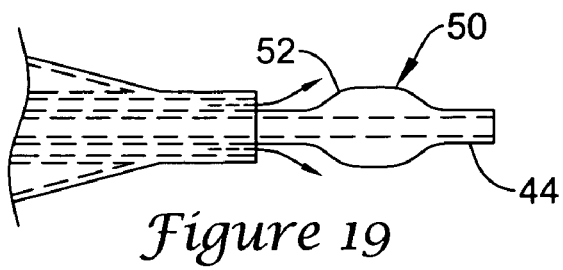
FIG. 19 is a fragmentary side elevational view of an alternate embodiment having the axially displaceable guidewire tube advanced to valve the distal end of catheter open.

FIGS. 18–19 illustrate another embodiment for controlling, metering, and occluding flow through the main axial orifice at the distal end of the discharge lumen 40. These two figures show a radially expanded portion 50 of the displaceable guidewire tube 44 which is located proximate the distal end of the discharge lumen 40. It will be understood that, with this embodiment, the gate biased to a closed position, as described hereinbefore, would not be employed. Rather, the discharge lumen would be maintained with a constant cross-section. In this embodiment, it will be understood, the radially expanded portion 50 of the displaceable guidewire tube 44 would be larger than the main axial orifice in the discharge lumen 40. Consequently, when the displaceable guidewire tube 44 is retracted to a position as illustrated in FIG. 18, a shoulder 52 defined by the expanded portion of the displaceable guidewire tube 44 would engage the distal end of the discharge lumen 40 to occlude egress flow of perfused fluid through the main axial orifice. When such flow is precluded, the perfused blood will pass through the side wall orifices 26, 27 and reduce trauma during catheter withdrawal or advancement.

On the other hand, when the displaceable guidewire tube 44 is extended so that the expanded portion 50 thereof is spaced from the distal end of the discharge lumen 40, as seen in FIG. 19, egress flow through the main axial orifice will be permitted. It will be understood that, the greater the distance the expanded portion 50 of the displaceable guidewire tube 44 is spaced from the distal end of the discharge lumen 40, the greater the flow of blood through the main axial orifice will be. The closer the expanded portion 50 of the displaceable guidewire tube 44 is brought to the discharge lumen distal end, the more egress flow through that orifice will be restricted. The mechanism illustrated in, and described with reference to, FIGS. 16 and 17 can also be employed for controlling the positing of the displaceable guidewire tube 44 relative to the discharge lumen 40.

FIGS. 20–22 illustrate another structure by which the valving of the distal and of the discharge lumen 40 can be accomplished. In this embodiment, an elastomeric element 64 is mounted at a desired axial location along the displaceable guidewire tube 44. The location is dictated by a disposition at which the elastomeric element 64 will occlude the distal end of the discharge lumen 40.

FIG. 21 illustrates the elastomeric element 64 which can be used in combination with a two-part displaceable guidewire tube 44. The distal end 66 of the elastomeric element is shown as being fixedly attached to an inner tube member 90 of displaceable guidewire tube 44. A proximal end 68 of the elastomeric element 64 is, in turn, fixedly attached to an outer tube member 92 of the displaceable guidewire tube 44. The inner tube member 90 and outer tube member 92 are selectively telescopable relative to one another. As will be able to be seen then, as inner tube member 90 is urged outwardly relative to outer tube member 92, the elastomeric element will be stretched longitudinally and will, concurrently, deform radially inwardly. On the other hand, if members 90, 92 are telescoped in an opposite relative relationship, the elastomeric element 64 will be deformed radially outwardly and achieve a configuration as seen in FIGS. 20 and 21. With the elastomeric element in such a configuration, the displaceable guidewire tube 44 can be withdrawn so that the element 64 engages the distal end of the discharge lumen 40 to occlude egress flow through the main axial orifice. It will be understood that any appropriate structure for effecting radially inward and outward deformation of elastomeric element 64, such as the use of a push wire, connected to either the distal or proximal end of the elastomeric element, is within the scope of the invention.

FIGS. 23 and 24 illustrate another embodiment of a valving mechanism. In this embodiment both distal and proximal ends 72, 74 of the valving element 70 are secured, in any appropriate manner, to the displaceable guidewire tube 44. The valving element 70 of this embodiment can, normally, be in a flaccid state. The element 70 can, however, be inflated, selectively, by actuation of means not shown. When inflated, the element 70 takes a form and size so as to be able to occlude the main axial orifice at the distal end of the discharge lumen 40. It will be understood that, with this embodiment, no relative axial movement of the displaceable guidewire tube 44 need be accomplished, since the radial dimension of the element 70 is not dependent upon axial movement of the displaceable guidewire tube 44.

FIGS. 25 and 26 illustrate another valving embodiment. In this embodiment, a sleeve 76 is mounted at a desired axial location along the displaceable guidewire tube 44. The location and size and dimensions of the sleeve 76 are such that the sleeve, being mounted generally concentrically with regard to the displaceable guidewire tube 44, can, at a determined axial position of the displaceable guidewire tube 44, occlude the discharge lumen 40. The sleeve 76 is provided with a closed distal end 78 by which it is mounted to the displaceable guidewire tube 44. The opposite, proximal end 80 of the sleeve 76 is open so that blood perfused through the perfusion lumen 17 can fill an annular space 82 between the displaceable guidewire tube 44 and the sleeve 76. The sleeve 76 is defined by an outer wall 84 which has a cross section approximating the cross section of the discharge lumen 40. It is for this reason that, with the displaceable guidewire tube 44 at a designated axial location, occlusion of the main axial orifice at the distal end of the discharge lumen 40 can be afforded.

At least one port is formed in the outer wall 84 by which the sleeve 76 is defined. FIG. 25, however, shows a series of ports 86 formed in the wall 84. FIG. 25 shows a series of six ports 86. Two ports are formed in the wall 84 at 180° relative to one another. A second pair of ports are axially spaced and circumferentially displaced at 90° relative to the first pair of ports. A third pair of ports is again axially spaced from the second pair of ports and circumferentially displaced at 90°.

FIG. 25 illustrates all six ports 86 being formed in the wall 84 so that, with the axial positioning of the displaceable guidewire tube 44 shown, all six ports are occluded by the discharge lumen 40. FIG. 26, on the other hand, shows axial movement of the displaceable guidewire tube 44 sufficient to expose all of the ports 86 so that they are not covered by the discharge lumen 40. In this position of the sleeve 76, the ports 86 afford egress of perfused blood through the ports.

While it is desirable to have a large perfusion lumen cross section so as to maximize blood flow, it is also desirable to have a small overall balloon catheter cross section so as to allow for inserting the projecting tip and balloon past narrowed vessel regions. Several embodiments of the present invention address these conflicting goals.

FIGS. 28–31 illustrate an embodiment of the present invention having a guidewire lumen external to the perfusion lumen. A guidewire lumen 113 is illustrated in FIGS. 28 through 31 as being external to a perfusion lumen 117 and internal to a balloon inflation molded member 114. The cross section of perfusion lumen 117 may be seen in FIG. 30 free of any occlusion by guidewire lumen 113, resulting is a larger effective cross section for perfusion lumen 117, allowing for increased blood flow through perfusion lumen 117 relative to the flow possible if guidewire lumen 113 was within perfusion lumen 117.

FIGS. 28–31 also illustrate an embodiment of the present invention having a stepped down perfusion lumen. FIG. 31 illustrates perfusion lumen 117 having a perfusion lumen proximal end 102 and a perfusion lumen distal end 104. FIGS. 28, 30, and 31 show perfusion lumen 117 having a larger cross section at 30 than at section 31. The larger cross section at proximal end 102 presents a larger area for perfusion blood flow, thereby offering decreased resistance to flow. The decreased cross section at distal end 104 presents a smaller area for blood flow near distal end 104 rather than along the entire length of perfusion lumen 117. Having decreased cross section only in the distal part of perfusion lumen 117 rather than all of perfusion lumen 117 decreases the resistance to flow through lumen 117 relative to a perfusion lumen having the smaller cross section along its entire length.

The cross section of balloon head assembly 10 increases from terminus 29 to converging tip portion 28 to perfusion lumen distal end 104. By having distal end 104 smaller than proximal end 102, the distal portion of balloon head assembly 10 is small enough to enter narrow vessel regions not enterable by a head assembly having the larger cross section at proximal end 102. Using this embodiment, at least part of balloon envelope 16 may be brought to bear upon a narrow vessel region not enterable by entire balloon head assembly 10. After widening such a narrow stenotic region, head assembly 10 may be further advanced. In one embodiment of the invention decreasing cross section region 112 is a step decrease. In another embodiment, region 112 is a tapered decrease. In yet another embodiment, region 112 runs the entire length of perfusion lumen 117.

Perfusion lumen 117 may be formed of a flexible material 21 such as polyamide elastomer or urethane. In one embodiment, helical members 20 may be formed from a metallic ribbon. In another embodiment helical members 20 may be formed of stainless steel. Balloon inflation molded member 114 may be formed from polyamide elastomer, polypropylene or polyethylene for example, or otherwise molded of any suitable material. Guidewire lumen 113 may be formed of polyethylene or any other suitable material.

FIGS. 32–34 illustrate an embodiment of the invention having an inflatable perfusion lumen 217. In these figures, lumen 217 is shown in an inflated position. When lumen 217 is in a deflated position, it can be compressed within balloon 16. Guidewire lumen 213 is shown external to inflatable perfusion lumen 217 and internal to balloon inflation molded member 214. FIG. 32 illustrates perfusion lumen 217 having inflatable helical members 106 attached to flexible material 21. Inflatable helical members 106 are in fluid communication with a perfusion lumen inflation lumen 108. The embodiment illustrated in FIG. 32 is seen to have two inflatable and therefore deflatable elements, balloon 16 and perfusion lumen 217. A tip stiffener (not shown) may be fixed near perfusion lumen distal end 104 to support perfusion lumen 217 against longitudinal collapse. Guidewire lumen 213 may be constructed of materials to stiffen it against longitudinal collapse and the tip stiffener may be connected thereto.

With both balloon envelope 16 and inflatable helical members 106 deflated, balloon head assembly 10 has a small deflated cross section, allowing for insertion into otherwise unreachable narrow vessel regions. With deflated head assembly 10 inserted into a narrow stenotic vessel region, inflation fluid is injected into perfusion lumen inflation lumen 108, the inflation fluid flowing into inflatable helical members 106, thereby inflating and providing support for perfusion lumen 217. With perfusion lumen 217 inflated, balloon envelope 16 may be inflated to widen the stenotic region while inflated perfusion lumen 217 provides radial outward support against the inward radial force of inflated balloon envelope 16. Providing for an inflatable perfusion lumen allows for a small balloon assembly cross section during insertion, when a small cross section is needed, and allows for a larger perfusion lumen cross section during balloon inflation, when blood perfusion is needed. In one embodiment, the balloon inflation lumen and perfusion lumen inflation lumen are separate. In yet another embodiment, the balloon inflation lumen and perfusion lumen inflation lumen are common.

FIGS. 35–38 illustrate an embodiment of the present invention having both a stepped down perfusion lumen 217 and a collapsible guidewire lumen 313. Collapsible guidewire lumen 313 is preferably formed from a polyamide elastomer, a polyolefin ionomer such as Surlyn⊕, polyamideimide, or other suitably flexible material. Balloon inflation lumen molded member 114 is shown external to both perfusion lumen 217 and guidewire lumen 314. The stepped down perfusion lumen 217 is discussed with respect to FIG. 28.

FIG. 35 illustrates guidewire lumen 313 running through balloon head assembly 10 internal to perfusion lumen 217. Guidewire lumen 313 is best seen is FIGS. 36 through 38 in un-collapsed position A and collapsed position B.

In use, balloon head assembly 10 is advanced onto a narrowed stenotic vessel region. When the treating physician has placed the balloon across the lesion, guidewire 42 (not shown) is backed out of guidewire lumen 313, causing guidewire lumen 313 to collapse, increasing the cross sectional area in perfusion lumen 217 available for blood flow. FIGS. 37 and 38 illustrate guidewire lumen 313 in collapsed position B and un-collapsed position A and the available flow area in perfusion lumen 217 when lumen 313 is in each position.

A collapsible guidewire lumen provides the advantage of increasing the unoccluded cross-section of the perfusion lumen when the guidewire is not needed. The sequence of catheter insertion, balloon inflation, and guidewire removal discussed above are illustrative only, not exhaustive.

Obviously many modifications and variations of the present invention are possible in light of the above teachings. For example, while some material preferences have been indicated, any suitable material may be employed. Also, while a preferred array of discharge orifices is discussed above, other arrays of elongated discharge orifices may be employed to facilitate perfusion discharge. Indeed, the several teachings herein may be usefully employed in other perfusion applications. It is therefore to be understood that, within the scope of this appended claims, the invention may be practiced otherwise than as specifically described.

What is claimed is:

1. A balloon angioplasty catheter comprising:
   an elongated catheter body having a proximal end and a distal end;
   a balloon including an inflatable envelope portion, the balloon having a proximal end and a distal end;
   a tubular member defining a perfusion lumen extending through the balloon, the perfusion lumen having a proximal end and a distal end, the proximal end of the perfusion lumen being proximate the proximal end of the balloon, the perfusion lumen decreasing distally in cross section within the inflatable envelope portion; and
   wherein the tubular member includes a metallic ribbon coil support.

* * * * *